United States Patent
Bianchini et al.

(10) Patent No.: US 9,810,966 B2
(45) Date of Patent: Nov. 7, 2017

(54) RANDOM ACCESS STIMULATED EMISSION DEPLETION (STED) MICROSCOPY

(71) Applicants: FONDAZIONE ISTITUTO ITALIANO DI TECNOLOGIA, Genoa (IT); BAYLOR COLLEGE OF MEDICINE, Houston, TX (US)

(72) Inventors: Paolo Bianchini, Genoa (IT); Peter Saggau, Houston, TX (US); Alberto Diaspro, Genoa (IT)

(73) Assignees: FONDAZIONE ISTITUTO ITALIANO DI TECNOLOGIA, Genoa (IT); BAYLOR COLLEGE OF MEDICINE, Houston, TX (US)

( * ) Notice: Subject to any disclaimer, the term of this patent is extended or adjusted under 35 U.S.C. 154(b) by 98 days.

(21) Appl. No.: 14/778,217

(22) PCT Filed: Mar. 21, 2014

(86) PCT No.: PCT/IB2014/060024
§ 371 (c)(1),
(2) Date: Sep. 18, 2015

(87) PCT Pub. No.: WO2014/147590
PCT Pub. Date: Sep. 25, 2014

(65) Prior Publication Data
US 2016/0274439 A1 Sep. 22, 2016

(30) Foreign Application Priority Data

Mar. 22, 2013 (IT) .............................. TO2013A0229

(51) Int. Cl.
*G02B 21/00* (2006.01)
*G02F 1/33* (2006.01)
(Continued)

(52) U.S. Cl.
CPC ........... *G02F 1/33* (2013.01); *G01N 21/6456* (2013.01); *G02B 21/002* (2013.01);
(Continued)

(58) Field of Classification Search
CPC ... G02F 1/33; G02B 21/0076; G02B 21/0092; G02B 21/0036; G02B 21/002; G02B 21/16
See application file for complete search history.

(56) References Cited

U.S. PATENT DOCUMENTS

| 4,405,237 A * | 9/1983 | Manuccia ................ G01J 3/44 356/301 |
| 5,883,734 A * | 3/1999 | Suzuki ..................... G02F 1/33 359/285 |

(Continued)

*Primary Examiner* — Ricky Mack
*Assistant Examiner* — Robert E Tallman
(74) *Attorney, Agent, or Firm* — Arent Fox LLP

(57) ABSTRACT

Optical scanning system, comprising an optical system for guiding a first and a second light beam, and deflector devices for deflecting first and second light beams in a directionally variable manner. The deflector devices comprise at least one acousto-optic deflector, and the optical system is arranged in such a way that the first and second light beams are counter-propagating through the acousto-optic deflector, which is controllable for deflecting the first and second light beams simultaneously or in pulse sequence. STED microscopy apparatus comprising an optical scanning system based on acousto-optic deflectors.

8 Claims, 3 Drawing Sheets

(51) Int. Cl.
*G02B 21/16* (2006.01)
*G02B 27/58* (2006.01)
*G01N 21/64* (2006.01)
*G02B 27/09* (2006.01)

(52) U.S. Cl.
CPC ..... *G02B 21/0036* (2013.01); *G02B 21/0076* (2013.01); *G02B 21/0092* (2013.01); *G02B 21/16* (2013.01); *G02B 27/58* (2013.01); *G02B 27/09* (2013.01)

(56) References Cited

U.S. PATENT DOCUMENTS

| | | | |
|---|---|---|---|
| 2007/0159690 A1* | 7/2007 | Ulrich | G02B 21/0032 359/385 |
| 2009/0219607 A1* | 9/2009 | Saggau | G02B 21/06 359/305 |
| 2012/0069332 A1* | 3/2012 | Frankel | G01J 3/10 356/301 |

* cited by examiner

RANDOM ACCESS STIMULATED EMISSION DEPLETION (STED) MICROSCOPY

The present invention relates to imaging techniques and more specifically high-speed and super-resolution microscopy techniques able to resolve details below the Abbe diffraction limit.

Among the techniques developed hitherto for the study of biological materials, multi-photon (MP) microscopy has become an essential tool for imaging such materials. Combined with disease-related transgenic animal models and genetically encoded or molecular fluorescent probes of cellular functions, such as voltage-sensitive or calcium-sensitive indicators, MP microscopy is currently considered to be the best means for studying live brain tissue.

Neurons communicate information via millisecond-range variations of their membrane potential. The recording of brain activity requires a microscopy technique which is able to work on different spatial scales, in three dimensions and with a high temporal resolution. In fact, even considering the activity of a single neuron, the neuronal signal is differently distributed in space and time across the dendritic and axonal segments.

It has been shown that some large-scale aspects of the brain functions may originate from the electrical properties of the individual neurons. Nevertheless closely spaced neurons can have vastly different activity patterns, while well-separated cells may belong to the same functional circuit, influencing each other via long axonal processes. Therefore an efficient method for systematically analyzing brain functions requires the simultaneous monitoring of the electrical activity of many cells throughout a brain volume.

Several technologies have been developed for carrying out rapid three-dimensional (3D) measurements on brain tissue, including fast liquid lenses, deformable mirrors, temporal and spatial multiplexing, axicon or planar illumination-based imaging, holographic scanning, and piezo-scanning with sinusoidal and non-linear resonance. Inertia-free acousto-optic deflectors (AODs) have been used to perform random-access imaging and rapidly vary focusing of a laser beam without mechanical movements, as described in US 2007/0201123. The combination of MP microscopy with this form of two-dimensional (2) or three-dimensional (3D) beam scanning (random-access multi-photon microscopy—RAMP) represents one of the best suited approaches to study brain functioning.

Despite its intrinsic advantage of optical sectioning, MP microscopy has a spatial resolution which is limited by diffraction and suffers from the drawback of a relatively high excitation wavelength value. Thus, the spatial resolution of RAMP microscopy has yet to be improved, without however affecting its high temporal resolution.

At present, one of the best methods for overcoming the diffraction limitation and increasing the spatial resolution of fluorescence microscopy is the stimulated emission depletion (STED) technique. The basic principle of such a method is based on the inhibition of spontaneous fluorescence emission at predefined coordinates of the sample, such that adjacent elements emit sequentially over time by means of a stimulated emission process. The most general STED architecture employs a regularly focused excitation laser beam overlaid on a second laser beam of a different wavelength inducing stimulated emission and has at least one zero-intensity point, e.g. a toroidal focal shape.

In 2009 photon STED microscopy technique was proposed, this combining the advantages of two-photon excitation (2PE) with the super-resolution of STED. A recent development in STED microscopy employs the same wavelength for both two-photon excitation and one-photon depletion, thus simplifying both the design and the image formation scheme of such super-resolution microscopes (see US 2009/0121153 and US 2011/0031411).

One object of the present invention is to provide a scanning system for a super-resolution microscopy or lithography apparatus allowing, respectively, the study of high-speed phenomena or the production of nano-structured objects.

Another object of the invention is to provide an optical scanning system able to direct in a rapidly variable manner the focus of two light beams onto a plurality of predefined positions within a given volume.

These and other objects are achieved according to the invention by an optical scanning system comprising:
  an optical system for guiding a first and a second light beam, and
  deflecting means for deflecting said first and second light beams in a directionally variable manner,
  wherein said deflecting means comprise at least one acousto-optic deflector, and said optical system is arranged in such a way that said first and second light beams are counter-propagating through said at least one acousto-optic deflector, said at least one acousto-optic deflector being controllable for deflecting, simultaneously or in pulse sequence, said first and second light beams.

Although the present invention has been devised specifically in relation to the field of fluorescence microscopy and functional imaging of the brain tissue, it may in fact have a utility in other fields such as nanolithography, nanofabrication, optical information retrieval storage, and other fields involving high-speed phenomena.

According to the invention, the two beams enter the random-access scanning system from opposite sides and counter-propagate through each AOD element. This configuration exploits the maximum deflection efficiency of the AODs, should both the beams match the polarization requested by the AODs and both beams have the same wavelength; thus one acoustic control wave for each AOD element is sufficient. Depending on the number of AOD elements it is also possible to provide a system able to perform scanning in several directions: with as single AOD it is possible to perform a one-dimensional (1D) scan, while with 4 AODs it is possible to perform a three-dimensional (3D) scan.

In a preferred embodiment of the invention, the present invention relates to an apparatus for irradiating a target material in order to excite elements of an excitable chemical species contained within said target material to an excited state, comprising
  an optical scanning system according to the invention, wherein said first light beam is adapted to excite said elements to said excited state, and said second light beam is adapted to reduce the number of said excited elements in said excited state, and
  means for directing said first and second light beams onto said target material in such a way that said first and second light beams form respective, movable, partially overlapped, irradiation areas on said target material.

In a particularly preferred embodiment, the present invention proposes an optical scheme which combines RAMP technology and single wavelength two-photon excitation STED (SW 2PE-STED) technology, resulting in fast super-resolution microscopy which may be defined as "random-access stimulated emission depletion (RASTED) microscopy". Such a technique provides a method for super-resolution imaging of sites of interest in a sample without the relatively long time requirements of conventional raster scanning systems. Furthermore, such high-speed scanning is necessary for observing phenomena such as electric signal transmission in neurons.

Further characteristic features and advantages of the system according to the invention will become clear from the following detailed description of an embodiment of the invention, with reference to the accompanying drawings which are provided purely by way of a non-limiting example and in which.

Figure 1:
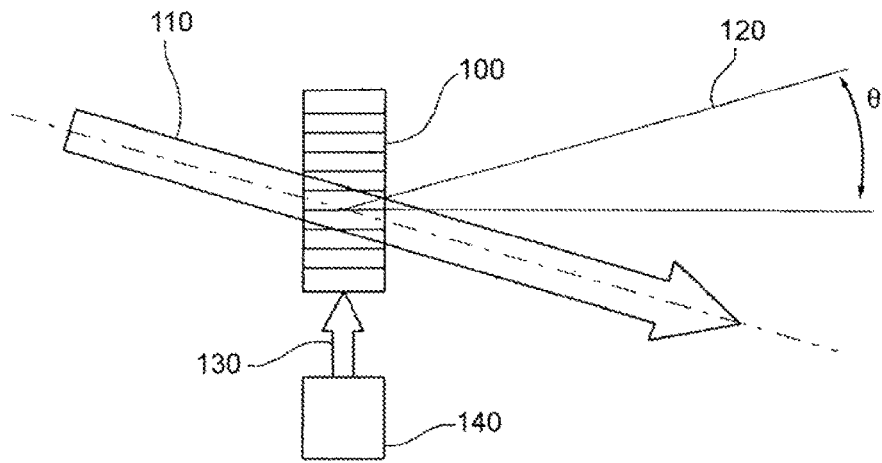
FIG. 1 is a schematic diagram of an acousto-optic deflector according to the prior art with a constant-frequency acoustic wave.
Figure 2:
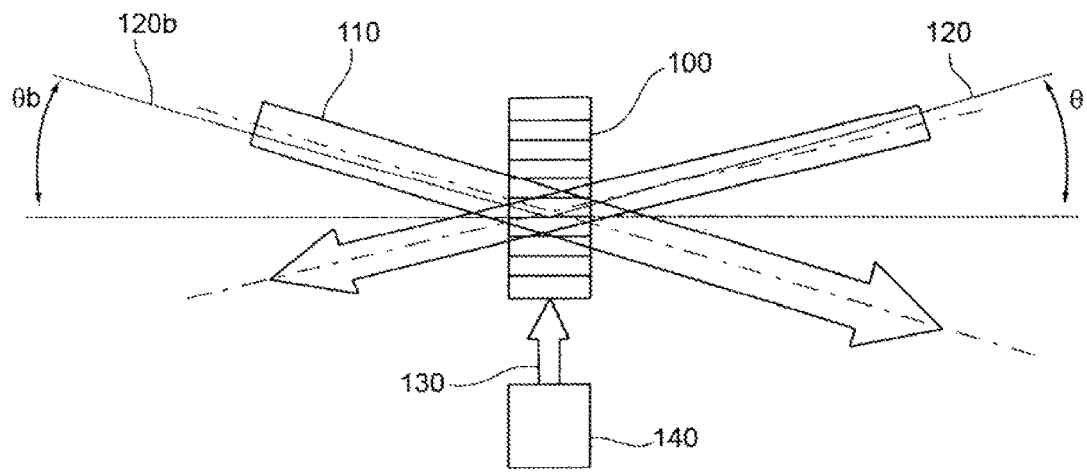
FIG. 2 is a schematic diagram of an acousto-optic deflector with a constant-frequency acoustic wave which deflects two counter-propagating light beams according to the invention.

With reference initially to FIG. 1, a driver device 140 creates an acoustic wave 130 which is transmitted through an acoustic-optic deflector (AOD) 100. The acoustic wave 130 has a constant frequency and is transmitted across the AOD 100. The AOD 100 also receives an incident light beam 110, a portion of which, indicated by 120, is diffracted or deflected as a result of the interaction between the light beam 110 and the acoustic wave 130. The deflected light beam 120 is deflected by an amount equal to the angle θ, which is dependent on the frequency of the acoustic wave 130 (a more detailed discussion of the principle is provided in US 2007/0201123 which is cited herein by way of a reference). Therefore, a variation of the frequency of the acoustic wave 130 varies the angle θ at which the incident beam is deflected. As dictated by the principle of conversation of the momentum, the deflected light beam 120 is deflected in the same direction as that in which the acoustic wave 130 propagates (i.e. away from the driving device 140).

Since the AOD 100 is symmetrical with respect to its direction of transmission, if a second light beam 110b enters into the AOD 100 on the opposite side to the first light beam 110, simultaneously or in a pulse sequence with respect to this first beam 110, a portion 120, 120b of each of the incident beams 110, 110b is diffracted or deflected as a result of the interaction between the acoustic wave 130 and the light beams 110 and 110b, at an angle θ and θb, respectively.

Figure 3:
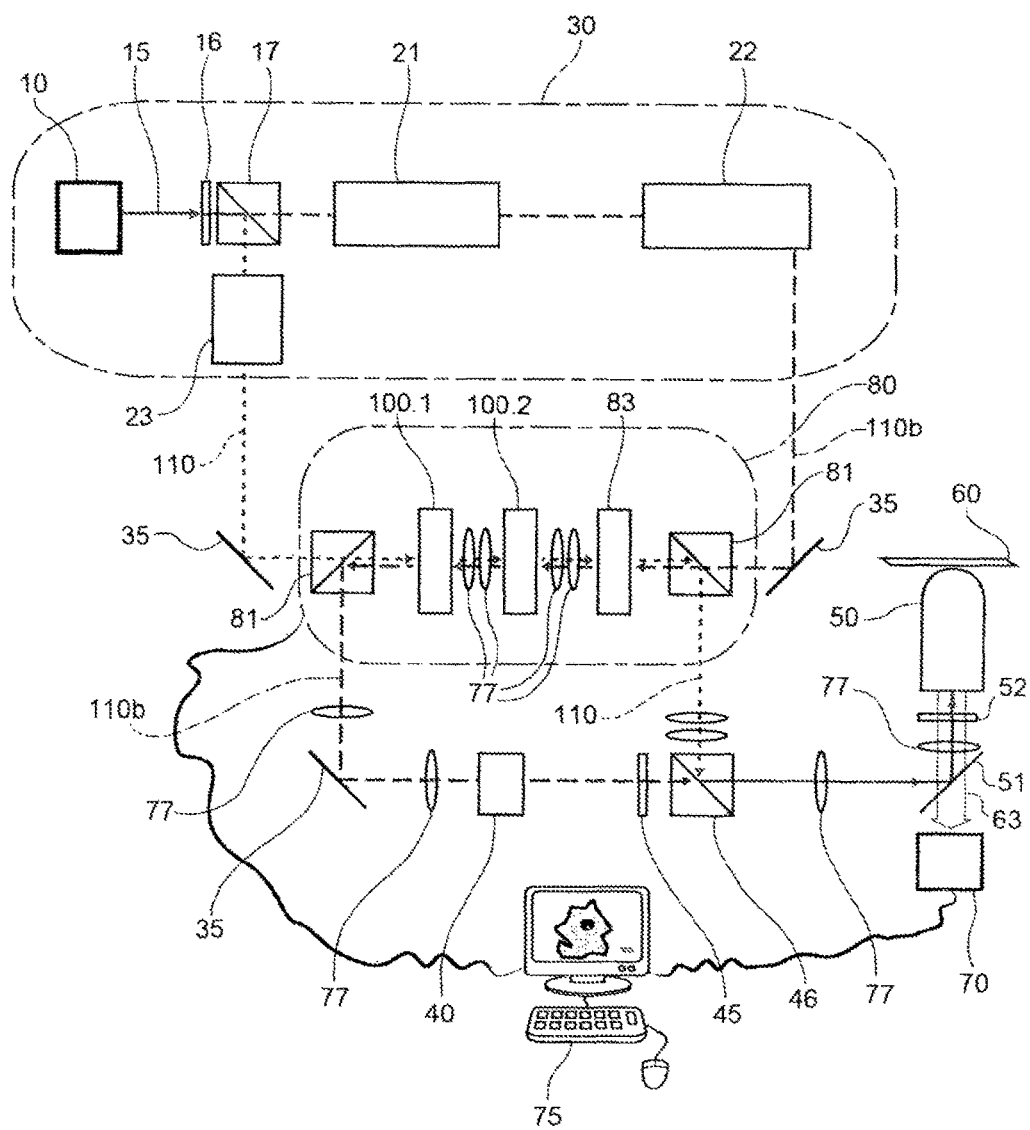
FIG. 3 is a schematic diagram or a preferred two-dimensional, random-access, multi-photon super-resolution STED microscope.

FIG. 3 shows a schematic illustration of the preferred random-access STED microscope.

The aforementioned microscope comprises a light source 10, in particular a laser source, for example a tunable pulsed ultrafast Ti:sapphire laser, operating at a repetition frequency of 80 Mhz with a pulse width of 140 fs. The source 10 emits a polarized light beam 15 which passes through a hall-wave plate 16 and then through a polarizing beam splitter 17 in order to obtain two light beams 110 and 110b. The first light beam 110 acts as a multi-photon excitation beam, while the second light beam 110b acts as a depletion beam. Since the pulses of the two beams must be synchronized when they reach the sample, a delay line 21 is provided along the optical path of the second light beam 110b. The second light beam 110b is furthermore lengthened by means of a pulse lengthening device 22 in order to reach a pulse length of 250 ps. Preferably, the lengthening device is realized by three 20 cm glass rods and a 100 m single-mode polarization-maintaining (PM) optical fibre; the output of the fibre is rotated so that the polarization thereof corresponds to that of the first light beam 110. However, other realizations of the lengthening device are possible, i.e. using gratings or prisms.

In order to perform pre-compensation of the temporal dispersion of the first light beam 110, a pre-chirping device 23 is arranged along the optical path of said beam. Preferably, such a device may be realized by means of a grating, but may also be based on prisms.

Preferably, the pulse length of the excitation beam is less than 1 ps, and in a particularly preferred manner is equal to 150 fs at the focal point; preferably, the pulse length of the depletion beam is greater than 50 ps and in a particularly preferred manner is in the range between 200 ps and 2 ns.

The aforementioned components form a generation block 30 which produces the two light beams with synchronizable pulses 110 and 110b having the aforementioned characteristics. As an alternative to a single laser source, the generation block may comprise a system with several sources.

Via two respective sets of mirrors 35, the light beams 110 and 110b enter in a two-dimensional random-access optical scanning system 80 based on acoustic-optic deflectors (AOD). The light beams 110 and 110b have the same polarization and the same wavelength and are combined in the scanning system by two polarizing beam splitters 81. Preferably, the first light beam 110 encounters a first AOD 100.1 intended for scanning along a predetermined x axis and than encounters a second AOD 100.2 which is rotated by 90 degrees, for scanning along the y axis, and then a spatial dispersion compensation element 81 which may be realized by means of a grating or another AOD, both rotated by 45 degrees. At this point the first light beam 110, upon exiting the scanning system 80 via the beam splitter 81, has a polarization which is orthogonal to that which it had upon entry into this system. For this reason, the scanning system 80 comprises an odd number of birefringent elements. However, since the spatial-dispersion compensation element 83 is rotated by 45 degrees, it comprises two half-wave plates with an AOD or a grating in between them. A more detailed discussion of a single-beam scanning system based on a series of AODs is provided in the description of US 2007/0201123 which is cited herein by way of a reference.

The second light beam 102 travels in the opposite direction to the first beam, passing through the three elements 100.1, 100.2 and 83 in reverse order, namely first through the element 83, then through the element 100.2 and finally through the element 100.1.

Figure 4:
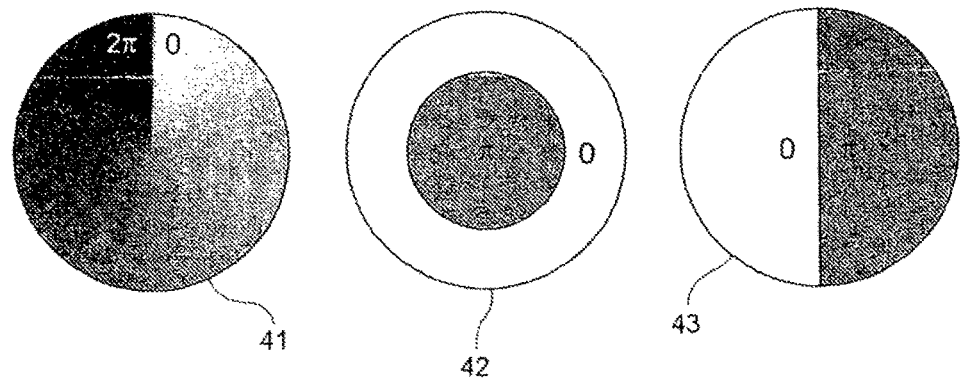
FIG. 4 shows a schematic illustration of a preferred phase mask to be applied to a beam shaping device in the microscope according to FIG. 3, in order to improve the resolution of the microscope.

The second light beam 110b which leaves the scanning system 8 passes through a beam-shaping device 40, preferably a vortex phase plate. Some known examples of phase masks are shown in FIG. 4; 41 denotes a vortex phase mask, 42 denotes a concentric phase mask, and 43 denotes a half-moon phase mask. These masks may be obtained with a phase plate or a spatial light modulator. The half-moon mask is preferably used in a 1D scanning system, while the concentric mask is used in a 3D scanning system. In any case all the combinations are possible.

The two light beams 110 and 110b are now combined by means of a half-wave plate 45, which rotates the polarization of the light beam 110b by 90 degrees, and a polarizing beam splitter 46. The combined beams, which now have a mutually orthogonal linear polarization, are directed towards an objective lens 50 via a short-pass beam splitter 51 and a quarter wave plate 52, so as to obtain a circular polarization of the light beams, and focused on a fluorescent sample 60. The fluorescent light 63 emitted by the sample is collected by the objective lens 50 and, after passing through the beam splitter 51 is acquired by a detector 70, which preferably is a photomultiplier tube.

The scanning system 80 is controlled by a compute 75 (which controls the respective driving device associated with each AOD), said computer also reconstructing and displaying the image acquired by the detector 70.

FIG. 3 also shows a lens system 77 which serves to position optically all the AODs and the phase mask in a conjugated plane.

Figure 5:
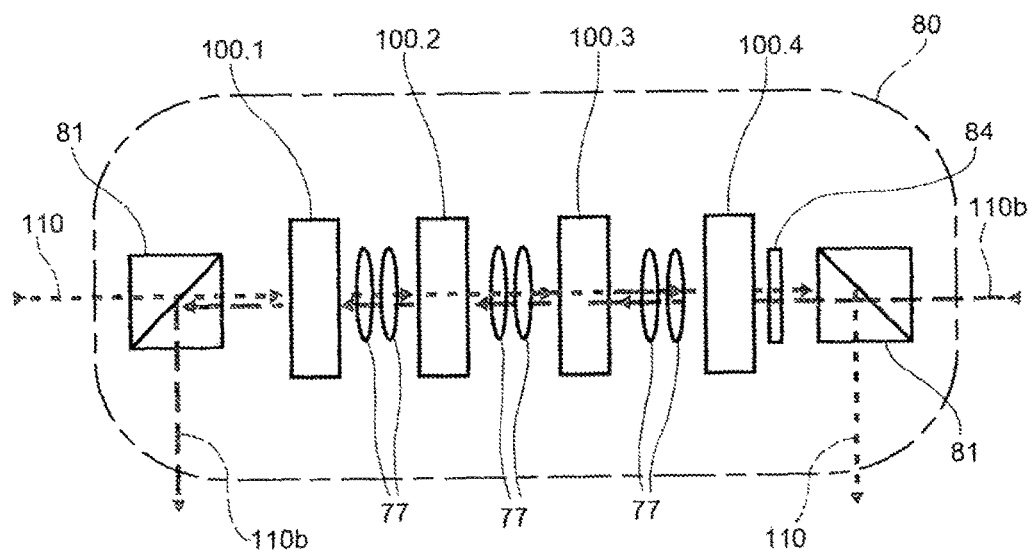
FIG. 5 is a schematic diagram of a preferred three-dimensional AOD scanning system.

FIG. 5 illustrates realization of three-dimensional random-access scanning unit. Parts which correspond to those shown in FIG. 3 have been indicated by the same reference numbers.

The realization shown in FIG. 5 comprises four AODs 100.1, 100.2, 100.3, 100.4 which are able to perform scanning with the focal spot of the two beams 110 and 110b in the lateral and axial directions, and also compensation of the spatial dispersion (see, in this connection, US 2007/0201123); a half-wave plate 84 is inserted in order to obtain an odd number of birefringent elements.

The invention claimed is:

1. Apparatus for irradiating a target material in order to excite elements of an excitable chemical species contained within said target material to an excited state, comprising
an optical scanning system comprising:
an optical system for guiding a first and a second light beam, and
a deflecting device for deflecting said first and second light beams in a directionally variable manner,
wherein said deflecting device comprises at least one acousto-optic deflector, and said optical system is arranged in such a way that said first and second light beams are counter-propagating through said at least one acousto-optic deflector, said at least one acousto-optic deflector being controllable for deflecting, simultaneously or in pulse sequence, said first and second light beams,
wherein said first light beam is constituted by a short-pulsed excitation beam and is adapted to excite said elements of an excitable chemical species to said excited state, and said second light beam is constituted by a long-pulsed depletion beam and is adapted to reduce the number of excited elements in said excited state, and
a directing system for directing said first and second light beams onto said target material in such a way that said first and second light beams form respective movable, partially overlapped, irradiation areas on said target material,
wherein the pulse length of the excitation beam is less than 1 ps, and wherein the pulse length of the depletion beam is longer than 50 ps.

2. Apparatus according to claim 1, wherein the wavelength of the excitation beam is within a spectral window where spontaneous fluorescence emission of the excitable chemical species is possible, and the multi-photon excitation fluorescence cross-section is not zero.

3. Apparatus according to claim 1, wherein the pulse length of the excitation beam is 150 fs at the focal point, and wherein the pulse length of the depletion beam is in the range between 200 ps and 2 ns.

4. Apparatus according to claim 1, wherein both the excitation beam and the depletion beam are linearly polarized upon entry into said optical scanning system.

5. Apparatus according to claim 1, comprising a beam-shaping device for shaping the depletion beam, arranged preferably in a conjugated plane after the optical scanning system and before a point where said first and second light beams are combined.

6. Apparatus according to claim 2, wherein the pulse length of the excitation beam is 150 fs at the focal point, and wherein the pulse length of the depletion beam is in the range between 200 ps and 2 ns.

7. Apparatus according to claim 3, wherein both the excitation beam and the depletion beam are linearly polarized upon entry into said optical scanning system.

8. Apparatus according to claim 4, comprising a beam-shaping device for shaping the depletion beam, arranged preferably in a conjugated plane after the optical scanning system and before a point where said first and second light beams are combined.

* * * * *